(12) United States Patent
Blomqvist (10) Patent No.: US 8,983,590 B2
(45) Date of Patent: Mar. 17, 2015

(54) MEDICAL DEVICE AND METHOD FOR DETERMINING A DYSSYNCHRONICITY MEASURE TECHNICAL FIELD

(75) Inventor: Andreas Blomqvist, Spånga (SE)

(73) Assignee: St. Jude Medical AB, Jarfalla (SE)

( * ) Notice: Subject to any disclaimer, the term of this patent is extended or adjusted under 35 U.S.C. 154(b) by 635 days.

(21) Appl. No.: 13/319,776

(22) PCT Filed: May 13, 2009

(86) PCT No.: PCT/SE2009/000244
§ 371 (c)(1),
(2), (4) Date: Nov. 10, 2011

(87) PCT Pub. No.: WO2010/131998
PCT Pub. Date: Nov. 18, 2010

(65) Prior Publication Data
US 2012/0059272 A1  Mar. 8, 2012

(51) Int. Cl.
*A61B 5/04* (2006.01)
*A61B 5/11* (2006.01)
*A61B 5/00* (2006.01)
*A61B 5/053* (2006.01)
*A61N 1/362* (2006.01)
*A61N 1/365* (2006.01)
*A61N 1/368* (2006.01)

(52) U.S. Cl.
CPC .............. *A61B 5/1102* (2013.01); *A61B 5/053* (2013.01); *A61B 5/0538* (2013.01); *A61B 5/6869* (2013.01); *A61N 1/3627* (2013.01); *A61N 1/36521* (2013.01); *A61N 1/3684* (2013.01)
USPC ....................................... 600/515

(58) Field of Classification Search
CPC ........ A61B 5/053; A61B 5/0538; A61B 5/11; A61B 5/1102; A61B 5/1107; A61N 1/3627; A61N 1/36521
USPC ............ 607/4, 5, 9, 17–18, 62; 600/508–508, 600/547
See application file for complete search history.

(56) References Cited

U.S. PATENT DOCUMENTS

| 6,044,294 | A | * | 3/2000 | Mortazavi et al. ............ 600/547 |
| 6,287,263 | B1 | * | 9/2001 | Briskin ........................ 600/526 |
| 7,092,759 | B2 | | 8/2006 | Nehls et al. |
| 7,440,803 | B2 | | 10/2008 | Ni et al. |
| 2002/0002389 | A1 | | 1/2002 | Bradley et al. |
| 2003/0105496 | A1 | | 6/2003 | Yu et al. |
| 2005/0038481 | A1 | | 2/2005 | Chinchoy et al. |

(Continued)

*Primary Examiner* — Brian T Gedeon
*Assistant Examiner* — Ankit Tejani (57) ABSTRACT

In an implantable medical device, such as a bi-ventricular pacemaker and a method for detecting and monitoring mechanical dyssynchronicity of the heart, a dyssynchronicity measure indicating a degree of mechanical dyssynchronicity of a heart of a patient is calculated. A first intracardiac impedance set is measured using electrodes placed such that the first intracardiac impedance set substantially reflects a mechanical activity of the left side of the heart and a second intracardiac impedance set is measure using electrodes placed such that the second intracardiac impedance set substantially reflects a mechanical activity of the right side of the heart. The measure of a dyssynchronicity is calculated based on a resulting parameter set from a comparison between at least a subset of the first and the second impedance sets, respectively, the subsets containing information of the mechanical systole, wherein a reduced dyssynchronicity measure corresponds to an improved synchronicity between the right side and the left side of the heart.

13 Claims, 8 Drawing Sheets

(56) References Cited

U.S. PATENT DOCUMENTS

| | | |
|---|---|---|
| 2005/0182447 A1 | 8/2005 | Schecter |
| 2007/0066905 A1* | 3/2007 | Zhang .......................... 600/509 |
| 2007/0191901 A1* | 8/2007 | Schecter ........................ 607/17 |
| 2007/0213778 A1 | 9/2007 | Burnes et al. |
| 2008/0234773 A1 | 9/2008 | Ni et al. |

\* cited by examiner

MEDICAL DEVICE AND METHOD FOR DETERMINING A DYSSYNCHRONICITY MEASURE TECHNICAL FIELD

BACKGROUND OF THE INVENTION

1. Field of the Invention

The present invention generally relates to implantable medical devices, such as pacemakers, and, in particular, to techniques for detecting and monitoring mechanical dyssynchronicity of the heart.

2. Description of the Prior Art

Current implantable cardiac resynchronization therapy (CRT) devices are designed to improve congestive heart failure symptoms in cardiomyopathy patients with electromechanical dyssynchrony. In particular, CRT devices are recommended for patients with prolonged QRS suggesting dyssynchronous heart activity. However, up to 30% of the patients carrying CRT devices do in fact not respond to the treatment, so called non-responders. This might depend on the fact that the there is discrepancy in the mechanical dyssynchrony and the electrical dyssynchrony, i.e. there is not a 100% correlation between the mechanical dyssynchrony and the electrical dyssynchrony. Today, in principle, all algorithms for pacing RV and LV in order to reduce or eliminate the dyssynchrony is based on electrical signals, with the exception for echo-cardiography or MR based technologies, which are unsuitable for implantable medical devices. Hence, the information acquired and used for reduction or elimination of the mechanical dyssynchrony is based solely on electrical dyssynchrony.

Figure 1:
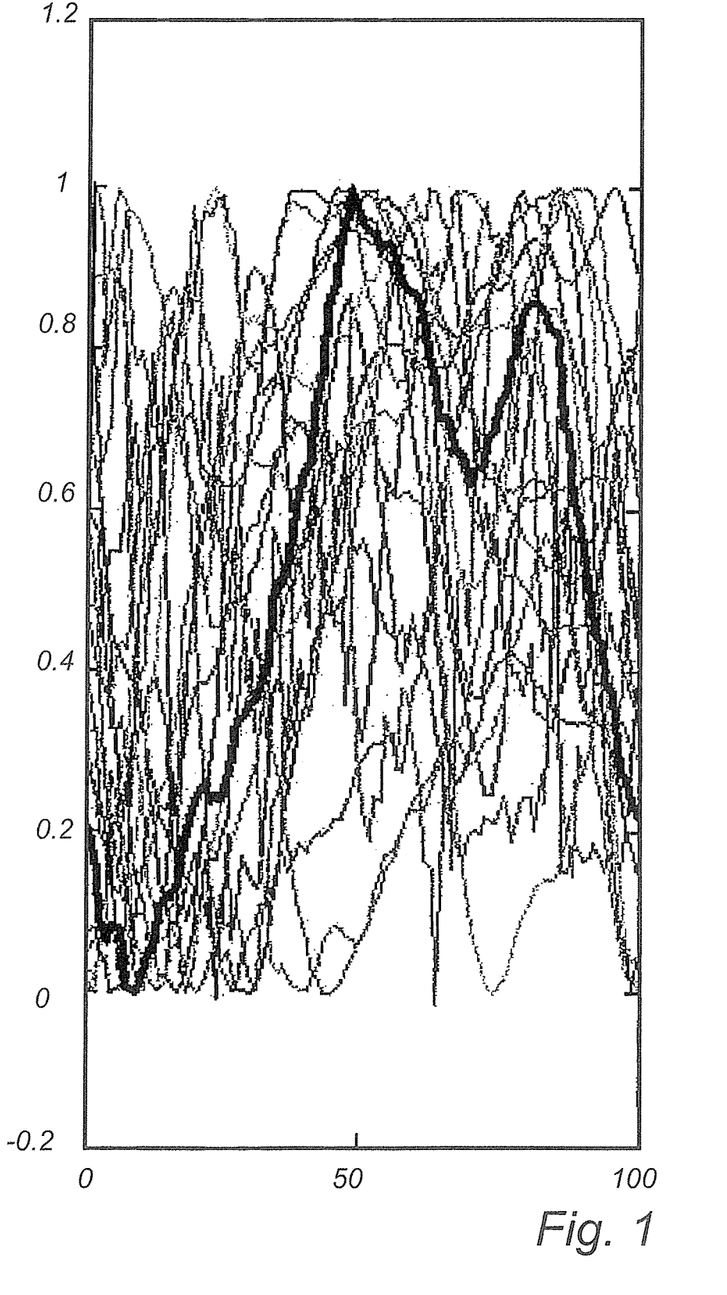
FIG. 1 is diagram showing impedance recordings from 19 different patients at the same body posture.

A large number of studies have shown that intra-cardiac impedance reflects the mechanical activity of the heart and thus provides a good basis for determining a mechanical dyssynchrony of a heart. However, intra-cardiac impedance is a very challenging parameter in that it, for example, varies significantly from patient to patient. The frequency content may for example vary greatly from patient to patient in spite of an identical filtering and signal processing, and the morphologies of the impedance signals may vary significantly. In addition, intra-cardiac impedance is very sensitive to the specific conditions during which the measurements were made such as the posture of the patient, the lead type and the lead position as well as to varying physiological parameters such as heart rate and respiratory rate. In FIG. 1 it is illustrated how measure intra-cardiac impedance may vary from patient to patient. It should be noted that the impedance is measured using the same measurement vector in each patient and for the same patient posture. All the waveforms shown in FIG. 1 are amplitude and time normalized and made up of ~30 second time averages and data from 19 patients is shown. The waveform indicated by the black, thick line is the ensemble average of all the other waveforms. Accordingly, despite the fact that intra-cardiac impedance is a very promising parameter for characterizing the mechanical activity of a heart there are a number of problems associated with measuring the impedance that have to be solved. The prior art discloses a number of approaches without presenting an adequate solution. For example, in US 2007/0191901 a cardiac resynchronization therapy (CRT) device using intra-cardiac impedance for determining systolic and diastolic cardiac performance is shown. US 2007/0191901 focus on gathering impedance data during, for example, myocardial thickening. In order to obtain a measure of the impedance data gathered during the myocardial thickening, the impedance is integrated from the onset of systole to time of peak contractility. Under conditions of normal or increased contractility this integrated value will have a greater value. Another measure of the cardiac performance discussed in US 2007/0191901 is a relation between the integral of the impedance over systole and the integral of the impedance over diastole. A larger area under the initial portion (during the systolic ejection phase) of the impedance curve will denote better systolic performance and a smaller area under the latter portion of the impedance curve will indicate more optimal lusitropic properties without regional post-systolic myocardial thickening. Thus, an optimized systolic and diastolic function will lead to an increased measure (i.e. the numerator will increase and the denominator will decrease) between the two integrals. The impedance information can be derived by acquiring the impedance between electrode pairs that transverse small myocardial segments. For example, measurements made between bipolar laterally positioned LV leads and the can of the device will reflect data more representative of lateral LV performance and electrodes placed in the interventricular septum or RVOT will generate data that reflects inter-ventricular septal ventricular performance.

Thus, significant efforts have been made within the art to develop devices and methods for detecting and monitoring mechanical dyssynchronicity of a heart. However, even though, as discussed above, intra-cardiac impedance constitutes a good basis for determining a mechanical dyssynchrony of a heart, one of the difficulties with providing a reliable measure of the dyssynchronicity of the heart is to overcome the problems with obtaining stable and reliable impedance data. Furthermore, in order to provide a reliable measure of the dyssynchronicity of the heart, the impedance data must also be processed in a proper and adequate way.

Consequently, there is still a need within art for an improved device and method that are capable of delivering a stable and reliable measure of a mechanical dyssynchrony of a heart of a patient.

SUMMARY OF THE INVENTION

An object of the present invention is to provide a medical device and a method that delivers a stable and reliable measure of a mechanical dyssynchronicity of a heart of a patient.

Another object of the present invention is to provide medical device and a method that delivers a robust measure of a mechanical dyssynchronicity of a heart of a patient that accurately quantifies a degree of dyssynchronicity.

According to a first aspect of the present invention, there is provided a medical device for determining a dyssynchronicity measure indicating a degree of mechanical dyssynchronicity of a heart of a patient. The medical device can be connected to at least two medical leads each including electrodes adapted to be positioned within or at the heart. Further, the device has an impedance measuring circuit adapted to measure a first intracardiac impedance set over at least one cardiac cycle using a first electrode vector/array including at least two electrodes placed such that the first intracardiac impedance set substantially reflects a mechanical activity of the left side of the heart, and to measure a second intracardiac impedance set over at least one cardiac cycle using a second electrode vector/array including at least two electrodes placed such that the second intracardiac impedance set substantially reflects a mechanical activity of the right side of the heart. Moreover, the device includes a calculating circuit adapted to calculate a measure of a dyssynchronicity based on a resulting parameter set from a comparison between at least a subset of the first and the second impedance sets, respectively, the subsets containing information of the mechanical systole.

According to a second aspect of the present invention there is provided a method for determining a dyssynchronicity measure in a medical device, the dyssynchronicity measure indicating a degree of mechanical dyssynchronicity of a heart of a patient. The medical device is connectable to at least two medical leads each including electrodes adapted to be positioned within the heart. The method includes the following steps: measuring a first intracardiac impedance set over at least one cardiac cycle using a first electrode vector/array including at least two electrodes placed such that the first intracardiac impedance set substantially reflects a mechanical activity of the left side of the heart, measuring a second intracardiac impedance set over at least one cardiac cycle using a second electrode vector/array including at least two electrodes placed such that the second intracardiac impedance set substantially reflects a mechanical activity of the right side of the heart; and calculating a measure of a dyssynchronicity based on a resulting parameter set from a comparison between at least a subset of the first and the second impedance sets, respectively, the subsets containing information of the mechanical systole, wherein a reduced dyssynchronicity measure corresponds to an improved synchronicity between the right side and the left side of the heart.

The present invention is based on the use of stable and reliable impedance data reflecting the mechanical activity of the left and right side of the heart, respectively, and on a new and inventive way of treating or processing this impedance data to create a measure of the mechanical dyssynchronicity that quantifies a degree of the mechanical dyssynchronicity. In order to achieve a stable and reliable measure of a dyssynchronicity between the left and right side of the heart it is of a high importance to obtain impedance data that mainly reflects the right side or the left side, respectively. That is, impedance data that provides a clean image of the mechanical activity of either the right side of the heart or the left side of the heart. Furthermore, the impedance data must be stable over time and between patients, or, at least, it must be possible to secure that the impedance data from a certain patient is reliable and repeatable. Therefore, the present invention is based on the idea of using measurement vectors that have been found to be stable and robust, in terms of repeatability between measurements of a patient during corresponding conditions and correlation between patients in a patient population and that, at the same time, essentially captures the mechanical activity of either the right or left side of the heart. The careful selection of suitable electrode vectors, which is one pillar upon which this invention rests, is founded upon thorough studies of the behaviour of intra-cardiac impedance measured at different patients and during different conditions.

Further, the present invention is based on the finding that a resulting parameter from a comparison between sets of intracardiac impedance reflecting mechanical activity of the right side of the heart and sets of intra-cardiac impedances reflecting mechanical activity of the left side of the heart accurately captures a degree of the synchronicity or dyssynchronicity of the mechanical activity between the right side and the left side of the heart. This resulting parameter can thus be used as a measure of the dyssynchronicity. The inventor has found that a reduction of the resulting parameter follows a reduction of the dyssynchronicity in magnitude and thus provides an effective measure of the degree of dyssynchronicity that is capable of quantifying a degree of the dyssynchronicity in an accurate manner.

According to an embodiment of the present invention, the resulting parameter between the first and the second sets of impedances is calculated as a difference value parameter set related to a morphology of the impedance sets, the difference value parameter set forming a waveform over the at least a part of a cardiac cycle. The waveform is integrated over a predetermined period of time of the part of a cardiac cycle to obtain an integral value, the predetermined period of time corresponding to a predetermined part of the mechanical systole. The dyssynchrony measure is determined to correspond to the integral value. The inventor has found that an integration of a set of difference values related to the morphology of the measured impedances sets (i.e. impedances measured by means of selected electrode vectors as described above) over a significant part of mechanical systole gives a parameter that accurately and reliably reflects the dyssynchronicity and follows the development of the dyssynchronicity. The part of mechanical systole over which the integration is performed is determined based on empirical data and it has been shown that a predetermined range of the heart cycle, for example, from the R-wave to the T-wave contains a significant part of the valuable information. Alternatively, a range between 20 and 50% of the cardiac cycle measured from the first activation of a ventricle has also been shown to comprise a significant part of the valuable information.

In an embodiment of the present invention, the measured or recorded first and second impedances sets, respectively, are synchronized in relation to a common reference cardiac event. That is, the impedance sets (i.e. one impedance set recorded by means of an measurement vector providing impedance data mainly reflecting the left side of the heart and one impedance set recorded by means of an measurement vector providing impedance data mainly reflecting the right side of the heart, respectively) are synchronized in relation to a specific cardiac event, for example, the P-wave. Both impedance waveforms are synchronized in relation to that specific observed reference event, which reference event will constitute the starting point or zero point for the waveforms.

In an embodiment of the present invention, an amplitude normalizing procedure may be performed on the first and second impedance sets. In some embodiments of the present invention, the first measurement vector may be quadropolar and the second vector may be bipolar, which may lead to a factor 100 difference in amplitude. By performing an amplitude normalizing procedure, for example, the calculation of the dyssynchronicity measure will be more accurate and also facilitated.

According to an embodiment of the present invention, each impedance sample of the first and second set or each value of the difference value parameter set are assigned with a predetermined weight. For example, each sample or value within the range 20-50% of the cardiac cycle can be assigned with the weight 1 and the samples or values being outside this range can be assigned with the weight 0. In another embodiment, only a few samples or even one sample is assigned with weights, i.e. in practice a very narrow range. For example, the sample corresponding to the opening of the aortic valve can be assigned with the weight 1 and the rest of the samples may be assigned with the weight 0. In yet another embodiment, the different weights are assigned to different ranges of the cardiac cycle. For example, samples between 25-45% are assigned with the weight 1, samples from 15-25% and 45-55% are assigned with the weight 0.5 the samples being outside these ranges are assigned with the weight 0.

In one embodiment of the present invention, a VV-interval can be optimized based on the dyssynchronicity measure. That is, based on the dyssynchronicity measure, the VV-interval can be adapted to achieve an optimal synchronization between the left ventricle and the right ventricle, wherein the dyssynchronicity measure is minimized. The pulse generator is thus instructed to adapt the VV-interval to obtain minimum dyssynchronicity measure. Further, the calculated dyssynchronicity measure may be compared with preceding dyssynchronicity measures obtain a trend of the dyssynchronicity measure and/or with a reference dyssynchronicity measure. It may be determined whether a present VV-interval should be extended or shortened based on the comparison and the pulse generator may be instructed to adapt a present VV-interval in accordance with the determined extension or shortening of the VV-interval.

In an embodiment of the present invention, the dyssynchronicity measure may be used to scan for so called non-responders before a CRT device is implanted. The impedance data may be measured by means of catheters provided with electrodes connected to the device or an extracorporeal device and the response to a certain CRT can be monitored and, if the patient responds, the CRT can be fine-tuned and optimized.

As those skilled in the art will appreciate, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

FIGS. 5a and 5b show the resulting parameter from a comparison between impedances mainly reflecting the mechanical activity of the left side and the right side, respectively, of the heart. FIG. 5a illustrates the waveform of the resulting parameter without CRT (cardiac resynchronization therapy) and FIG. 5b illustrates the same parameter at CRT.

DESCRIPTION OF THE PREFERRED EMBODIMENTS

The following is a description of exemplifying embodiments in accordance with the present invention. This description is not to be taken in limiting sense, but is made merely for the purposes of describing the general principles of the invention. Thus, even though particular types of implantable medical devices such as heart stimulators will be described, e.g. biventricular pacemakers, the invention is also applicable to other types of cardiac stimulators such as dual chamber stimulators, implantable cardioverter defibrillators (ICDs), etc.

Figure 2:
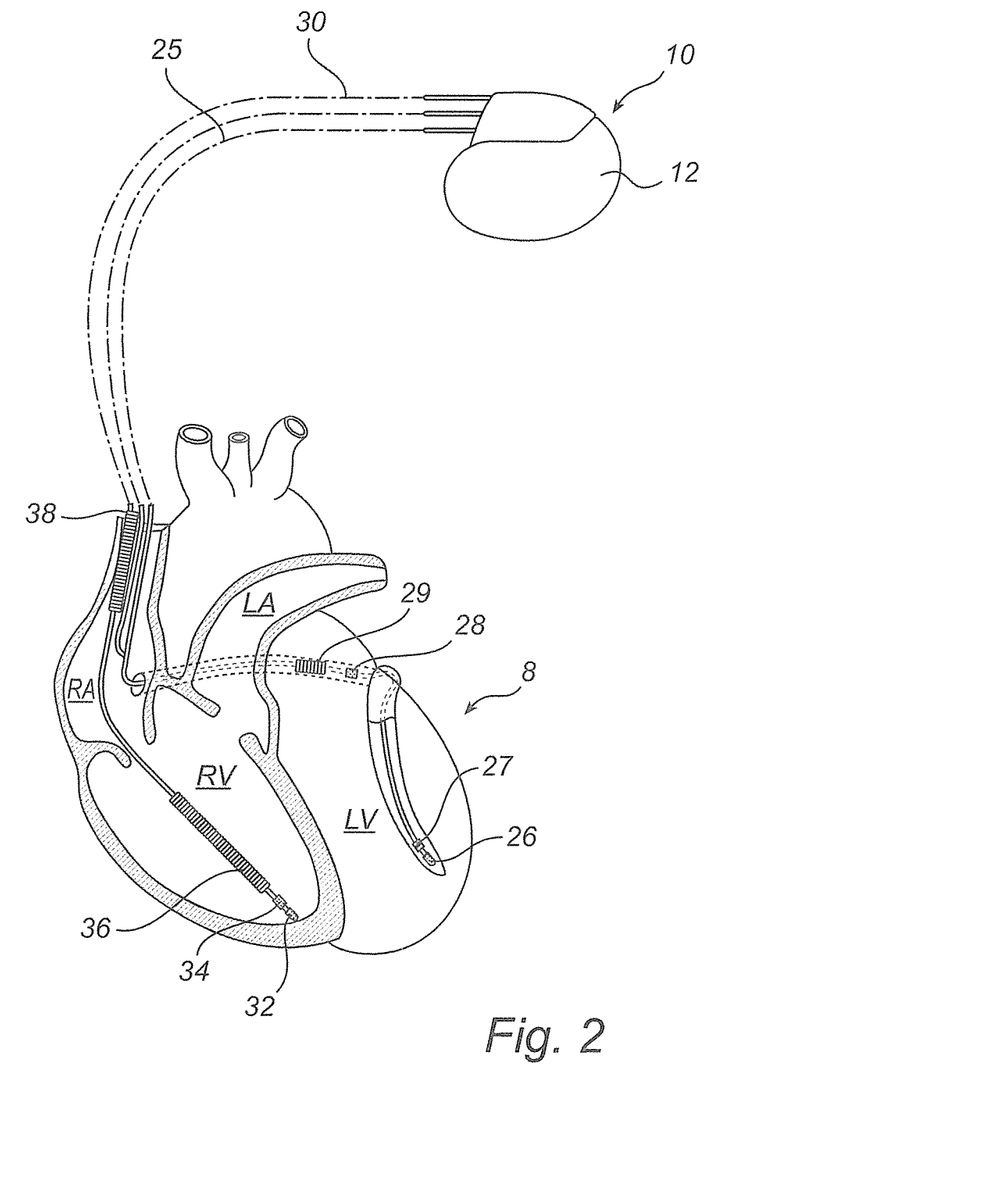
FIG. 2 is a simplified, partly cutaway view, illustrating an implantable medical device according to the present invention with a set of leads implanted into the heart of a patient.

With reference first to FIG. 2, there is shown an implantable medical device for determining a dyssynchronicity measure indicating a degree of mechanical dyssynchronicity of a heart of a patient according to an embodiment of the present invention. According to this embodiment, the invention is implemented in a stimulation device 10 having a case 12. The stimulation device 10 is in electrical communication with a patient's heart 1 by way of a right ventricular lead 30 having a right ventricular (RV) tip electrode 32, a RV ring electrode 34, RV coil electrode 36, and a superior vena cava (SVC) coil electrode 38. Typically, the RV lead is transvenously inserted into the heart 8 so as to place the RV coil electrode 36 in the right ventricular apex and the SVC coil electrode 38 in the superior vena cava. Accordingly, the right ventricular lead 30 is capable of receiving cardiac signals, and delivering stimulation in the form of pacing to the right ventricle RV.

In order to sense left atrial and ventricular cardiac signals and to provide left chamber pacing therapy, the stimulator 10 is coupled to a "coronary sinus" lead 25 designed for placement in the coronary sinus region via the coronary sinus for positioning a distal electrode adjacent to the left atrium. As used herein, the wording "coronary sinus region" refers to the vasculature of the left ventricle, including any portion of the coronary sinus, great cardiac vein, left marginal vein, middle cardiac vein, and/or small cardiac vein or any other cardiac vein accessible via the coronary sinus. Accordingly, the coronary sinus lead 25 is designed to receive atrial and ventricular pacing signals and to deliver left ventricular pacing therapy using at least a left ventricular (LV) tip electrode 26, a LV ring electrode 27 left atrial pacing therapy using at least a LA electrode 28 and a LA electrode 29. With this configuration biventricular therapy can be performed. Although only two medical leads are shown in FIG. 2, it should also be understood that additional stimulation leads (with one or more pacing, sensing, and/or shocking electrodes) may be used in order to efficiently and effectively provide pacing stimulation to the left side of the heart or atrial cardioversion. For example, a right atrium (RA) lead implanted in the atrial appendage having a RA tip electrode and a RA ring electrode may be arranged to provide electrical communication between the right atrium (RA) and the stimulator 10.

With reference to the configuration shown in FIG. 2, a number of impedances vectors can be used for impedance measurements to obtain impedance signals mainly reflecting the mechanical activity on the right side of the heart or the left side of the heart, respectively. For example, a current can be injected between the RV ring electrode 34 and the LV ring electrode 27 and the resulting impedance (voltage) can be measure between the RV tip electrode 32 and the LV tip electrode 26. The impedance signals measured by means of this vector will mainly reflect the mechanical activity on the left side of the heart. Other vectors that have been proven to deliver reliable and stable impedance measurement mainly reflecting the mechanical activity on the left side of the heart include:

Current injection: LV ring electrode 27 and LV tip electrode 26, and
Voltage measurement: LV ring electrode 27 and LV tip 26, or
Current injection: LV ring electrode 27 and RA ring electrode (not shown), and Voltage measurement: LV ring electrode 27 and RA ring electrode (not shown).

The latter vector will provide even more reliable and stable impedance signals if the LV lead is placed sufficiently low in the left ventricle, that is, more close to the apex as compared to the valve plane. It should be noted that these examples of measurement vectors are non-exhaustive.

In order to obtain stable and reliable impedance signals mainly reflecting the right side of the heart, the following vectors can be used:

Current injection: RV ring electrode 34 and RV tip electrode 32, and

Voltage measurement: RV ring electrode 34 and RV tip electrode 32, or

Current injection: RA ring electrode (not shown) and RV ring electrode 34, and Voltage measurement: RA tip electrode (not shown) and RV tip electrode 32, or Current injection: RV ring electrode 34 and case 12, and Voltage measurement: RV ring electrode 34 and case 12.

Figure 7:
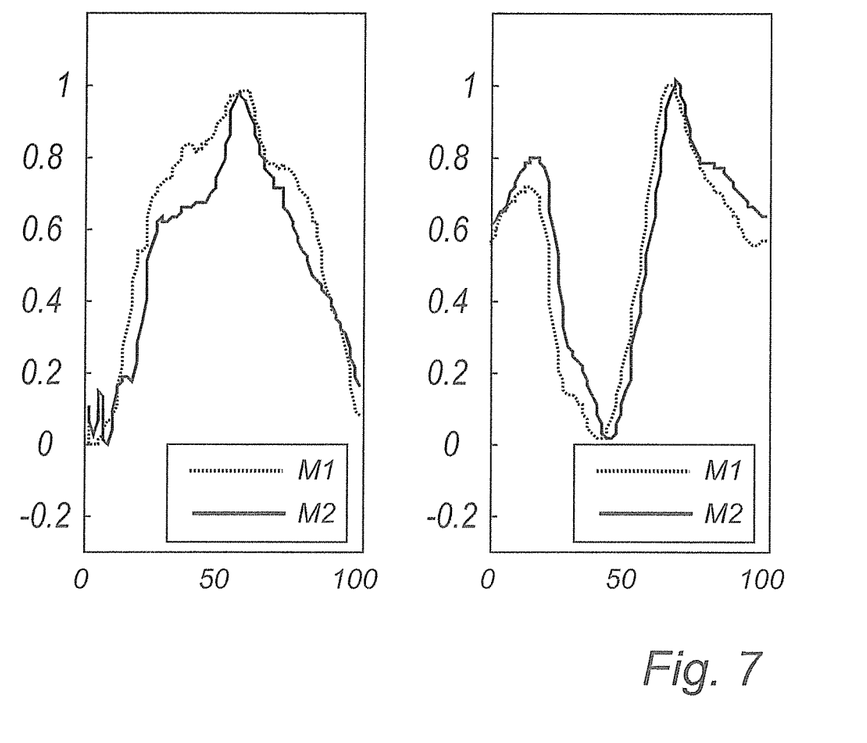
FIG. 7 shows diagrams of impedance waveform obtained from two different patients with a certain vector.

It should be noted that these examples of measurement vectors are non-exhaustive. Thus, although these configurations have been shown to provide good measurement results, it is understood that other configurations can be used and that the present invention is not limited to above-mentioned configurations provided that accurate and stable impedance signals are obtained, which may vary from patient to patient. To illustrate the importance of selecting configurations that provide accurate and stable impedance signals reference is being made to FIG. 7. In FIG. 7, two different examples of impedance measurement on patients are illustrated, where the left diagram shows an acceptable waveform and the right diagram shows a non-acceptable waveform, respectively. The measurements are conducted by means of a vector where the current is injected between a LV ring electrode and a RA ring electrode and are performed at two different points of time (M1 and M2). The left diagram illustrates the impedance signal reflecting mechanical activity on the left side of the heart during a cardiac cycle whereas the right diagram illustrates the impedance signal reflecting mechanical activity on the left side of the heart during a cardiac cycle. Accordingly, the selection of the measurement vectors to be used for a specific patient has to be made with carefulness.

Figure 3:
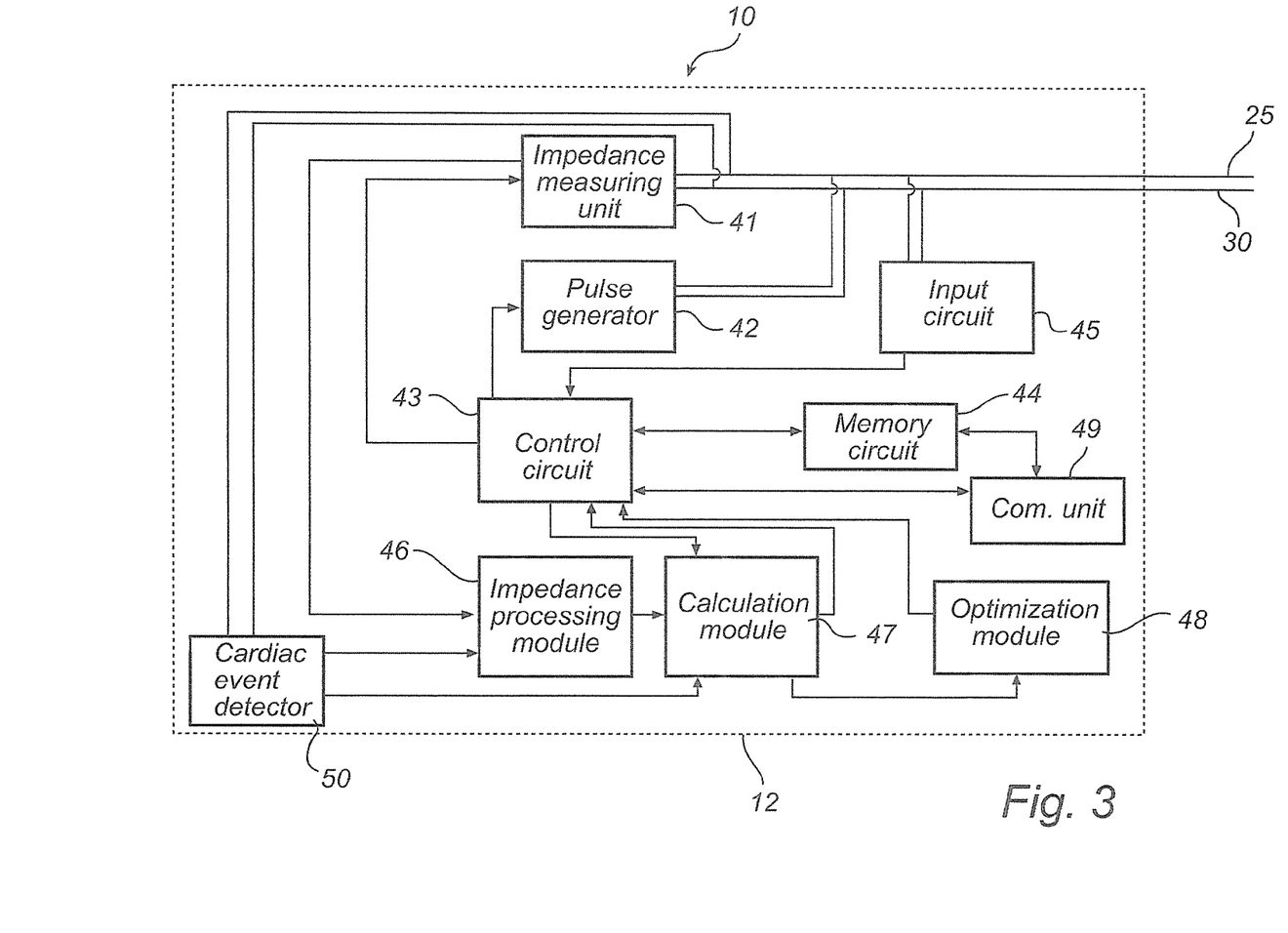
FIG. 3 is a functional block diagram form of the implantable medical device shown in FIG. 1, illustrating basic circuit elements that provide, for example, pacing stimulation in the heart and particularly illustrating components for calculating a dyssynchronicity measure according to the present invention.

Turning now to FIG. 3, the heart stimulator 10 of FIG. 2 is shown in a block diagram form. For illustrative purposes, reference is made to FIG. 2 for the elements of the leads that are intended for positioning in or at the heart. The heart stimulator 10 has a housing 12 that is hermetically sealed and biologically inert, see FIG. 2. Normally, the housing is conductive and may, thus, serve as an electrode. One or more pacemaker leads, where two are shown in FIG. 2, the left ventricle lead and the right ventricle lead 25 and 30, respectively, are electrically coupled to the implantable medical device 10 in a conventional manner. The leads 25, and 30 extend into the heart (see FIG. 2).

As discussed above with reference to FIG. 2, the leads 25, and 30 comprises one or more electrodes, such a coils, tip electrodes or ring electrodes, arranged to, inter alia, transmit pacing pulses for causing depolarization of cardiac tissue adjacent to the electrode(-s) generated by a pace pulse generator 42 under influence of a control circuit 43 comprising a microprocessor and for measuring impedances reflecting the septal wall movements. The control circuit 43 controls, inter alia, pace pulse parameters such as output voltage and pulse duration. A memory circuit 44 is connected to the control circuit 43, which memory circuit 44 may include a random access memory (RAM) and/or a non-volatile memory such as a read-only memory (ROM). Detected signals from the patient's heart are processed in an input circuit 45 and are forwarded to the microprocessor of the control circuit 43 for use in logic timing determination in known manner. The stimulator also includes a communication unit 49, for example, a telemetry unit or RF transceiver adapted for bi-directional communication with external devices.

Furthermore, an impedance measuring unit 41 is adapted to carry out impedance measurements of the intra-cardiac impedance of the patient, for example, by applying a current over the RV ring electrode 34 and the LV ring electrode 27 to measure impedance signals substantially reflecting mechanical activity on the left side of the heart. The resulting voltage is, according to these examples, measured between the RV tip electrode 32 and the LV tip electrode 26. In order to carry out impedance measurements of the intra-cardiac impedance of the patient substantially reflecting mechanical activity on the right side of the heart, a current may be applied over the RV ring electrode 34 and the RV tip electrode 32. The resulting voltage may be measured between the same electrode pair.

The raw impedance data are then supplied to an impedance processing module 46, which may include, for example, amplifiers and filters e.g. FIR or IIR filters. The impedance processing module 46 may further be adapted to perform, for example, amplitude normalizing and synchronization of the measured impedance sets in relation to a predetermined cardiac event. Moreover, the impedance sets may also be provided with predetermined weights in the impedance processing module 46.

A calculation module 47 is adapted to calculate a measure of a dyssynchronicity based on a resulting parameter set from a comparison between at least a subset of the first and the second impedance sets, respectively, which subsets contain information of the mechanical systole. The resulting set may alternatively be provided with weights, if this step was not performed in the impedance processing module 46.

In one embodiment, the calculation module 47 is adapted to calculate the resulting parameter between the first and the second sets of impedances as a difference value parameter set related to a morphology of the impedance sets, which difference value parameter set forming a waveform over the at least a part of a cardiac cycle, to integrate the waveform over a predetermined period of time of the part of a cardiac cycle to obtain an integral value, the predetermined period of time corresponding to a predetermined part of mechanical systole; and to determine the dyssynchrony measure to correspond to the integral value. This will be described in more detail below with reference to FIG. 4.

Furthermore, a cardiac event detector 50 is connectable to the electrodes, for example, the RV tip electrode 32, the RV ring electrode 34, the LV tip electrode 26, and the LV ring electrode 27 via the leads 25 and 30, and is connected to the impedance processing module 46 and the calculation module 47. The cardiac event detector 50 is adapted to detect the occurrence of cardiac events in the cardiac cycle. In one embodiment, the cardiac event detector 50 is adapted to identify a first predetermined event of the cardiac cycle, for example, the R-wave of a cardiac cycle, indicating a first activation of the left or the right ventricle. Further, a second cardiac event, for example, the T-wave of the cardiac cycle may be identified. The cardiac event detector 50 may also detect reference event for use in synchronization between the left side impedance sets (i.e. impedances reflecting mainly the left side of the heart) and right side impedance sets (i.e. impedances reflecting mainly the right side of the heart).

The calculation module 47 may further be adapted to determine a period of the cardiac cycle in relation to the identified events in the cardiac cycle over which the resulting parameter is calculated. In one embodiment, as will be explained in detail below, a dyssynchronicity measure is calculated by integration of the resulting parameter over a part of a cardiac cycle, which part corresponds to the most significant part of the mechanical systole and the period of time between the detection of an R-wave and the detection of a T-wave has been shown to entail that the significant part of the cardiac cycle can be captured. Alternatively, the integration can be performed over range between 20-50% of the heart cycle following the activation of the primary ventricle, a part that empirically has been shown to include the significant part of mechanical systole.

The implantable medical device 10 may further include an optimization module 48 connected to the calculation module 47 and the control circuit 43. In one embodiment of the present invention, a VV-interval is optimized based on the dyssynchronicity measure, wherein the dyssynchronicity measure is minimized. The pulse generator 42 is instructed to adapt the VV-interval in accordance with the optimization. In another embodiment, the optimization module 48 is adapted to compare a present dyssynchronicity measure with preceding dyssynchronicity measures to obtain a trend of the dyssynchronicity measure and/or with a reference dyssynchronicity measure to identify and to determine whether a present VV-interval should be extended or shortened based on the comparison. The pulse generator 43 is instructed to adapt a present VV-interval in accordance with the determined extension or shortening of the VV-interval. For example, a reference measure may be obtained for a patient in connection with the implantation of the device during synchronized ventricular activity.

Figure 4:
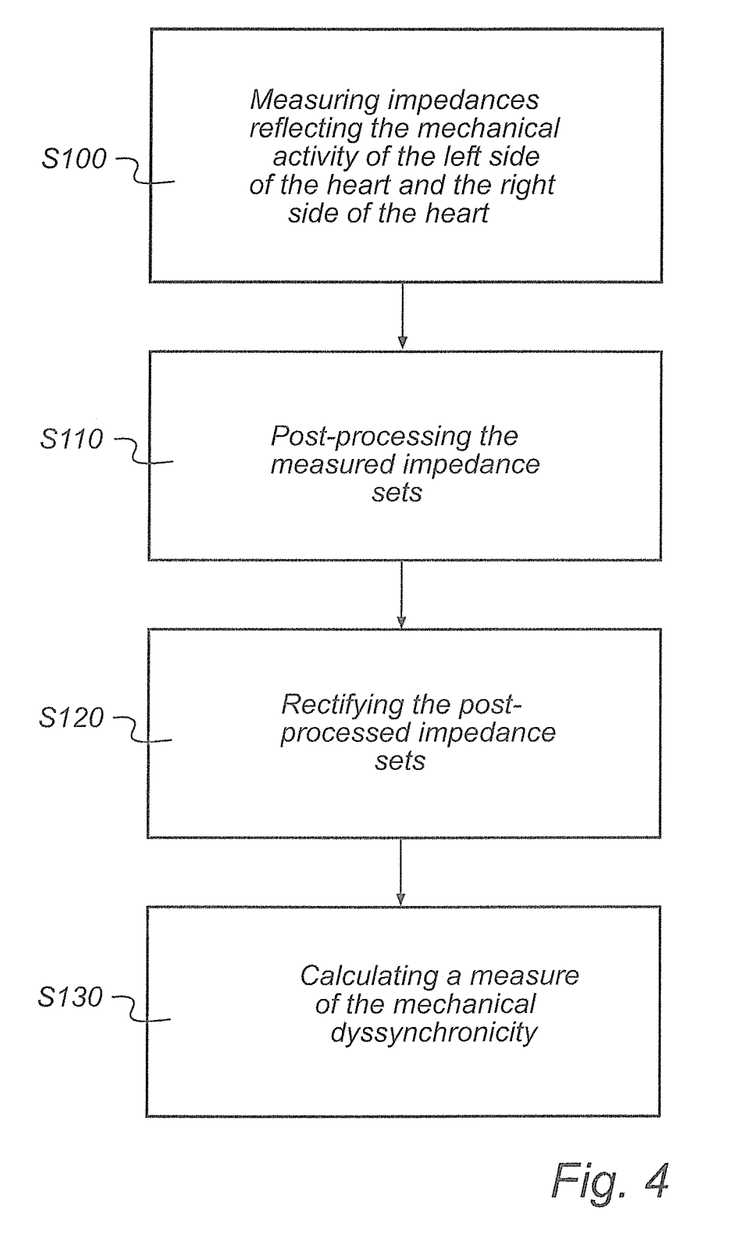
FIG. 4 is a flow chart describing the general principles of the method according to an embodiment the present invention.

With reference now to FIG. 4, an embodiment of the present invention will be described. First, at step S100, sets of impedance data $V_1$ is acquired in subsequent impedance measurement sessions. The impedances of the first impedance data set $V_1$ reflect mechanical activity at the left side of the heart and are measured by means of a first electrode vector or array. In one embodiment (see FIGS. 2 and 3), a current is injected by the current generating circuit of the impedance measuring circuit 41 between a RV-ring electrode 34 and a LV-ring electrode 27 and the resulting impedance is measured by a voltage measuring circuit of the impedance measuring circuit 41 between a RV-tip electrode 32 and a LV-tip electrode 26. The impedance data gathered by means of this electrode vector will thus mainly reflect the mechanical activity of the left side of the heart. Further, a second impedance data set $V_2$ reflecting mechanical activity at the right side of the heart is measured by means of a second electrode vector or array. The current is injected between the RV-tip electrode 32 and the RV ring electrode 34 and the resulting voltage is measured between the same electrode pair (see FIG. 2).

Thereafter, at step S110, the impedances of the first and second sets of data $V_1$ and $V_2$ are processed in the impedance processing module 46. This may include a step where the measured impedances can be amplitude normalized to even out amplitude differences caused by, inter alia, differences in electrode configurations. For example, using the electrode configurations discussed above may result in an amplitude difference of a factor of about 100 since the first vector quadropolar and the second vector is bipolar. Further, the processing step may also include a synchronization step to synchronize the two sets of impedance data $V_1$ and $V_2$ in time in relation to a common reference point, i.e. a reference cardiac event, for example, the P-wave.

The processed impedance data sets $\overline{V}_1$ and $\overline{V}_2$ might thereafter be assigned with predetermined weights in step S120, yielding and $\overline{V}_{1,weights}$ and $\overline{V}_{2,weights}$. In one embodiment of the present invention, the individual impedance values or samples are rectified, in the rectifying step S120, yielding the rectified impedance data sets $\overline{V}_{1,rect}$ and $\overline{V}_{2,rect}$. However, there are other conceivable embodiments as will be described below.

Thereafter, at step S130, a measure of a dyssynchronicity based on a resulting parameter set R from a comparison between at least a subset of the rectified impedance data sets $\overline{V}_{1rect}$ and $\overline{V}_{2rect}$ is calculated. In one embodiment of the present invention, the rectified data sets are subtracted to create a difference signal according to:

$$R = V_{Diff} = \overline{V}_{1rect} - \overline{V}_{2rect} \qquad (1)$$

Figure 5A:
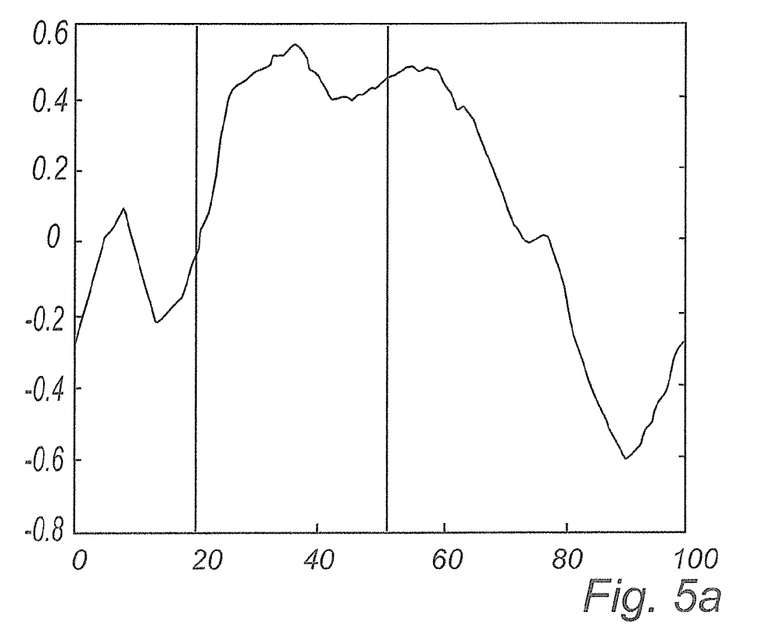

The resulting parameter R from the comparison between the rectified impedance data sets $\overline{V}_{1rect}$ and $\overline{V}_{2rect}$ is thus related to a morphology of the impedance sets and the resulting parameter set may form a waveform over at least a part of a cardiac cycle. This is illustrated in FIG. 5a.

Alternatively, the parameter set $V_{Diff}$ can be calculated from the impedance sets and then be assigned with the predetermined weighs. In other words, a modified step S130 ($R = V_{Diff} = \overline{V} - \overline{V}$) is performed before a modified step S120 is performed ($V_{Diff, weights}$).

The resulting parameter set R or $V_{Diff}$ is integrated over a part of a cardiac cycle, which part corresponds to the most significant part of the mechanical systole. Empirically, this significant part has been found to be in the range between 20-50% of the heart cycle following the activation of the primary ventricle. Thus, $V_{Diff}$ may be integrated in accordance with the following:

$$RDI = \int_{0.2}^{0.5} |V_{Diff}| dx \qquad (2)$$

According to another embodiment of the present invention, the period of time between the detection of an R-wave and the detection of a T-wave is selected for the integration, a selection of a period of time that also has been shown to entail that the significant part of the cardiac cycle can be captured.

In the weighting step, the impedance samples (or the resulting parameter $V_{Diff}$) between 20-50% of the heart cycle following the activation of the primary ventricle may be provided with the weight 1 and the remaining samples may be provided with the weight 0. Then, the difference signal $V_{Diff}$ (or $V_{Diff, weights}$) can be integrated over the significant part of mechanical systole according to:

$$RDI = \int |V_{Diff}| dx \qquad (3)$$

The resulting value, RDI, is determined to correspond to the dyssynchronicity measure. Due to the fact that the only a part of the samples (i.e. the samples between 20 and 50% of the cardiac cycle) are provided with the weight 1 and the remaining samples are provided with the weight 0, this will in practice integrate the $V_{Diff}$ (or $V_{Diff, weights}$) between 20 and 50% of the cardiac cycle.

In a further embodiment, the sample at the point of the heart cycle corresponding to the opening of the aortic valve is provided with the weight 1 and the remaining samples are assigned with the weight 0. In this case, the RDI value will be the value of that particular sample. There are other conceivable alternatives. For example, the samples between 25 and 45% of the cardiac cycle (e.g. from the first activation of a ventricle) can be assigned with the weight 1, the samples between 15 and 25%, and 45 and 55%, respectively, can be assigned with the weight 0.5 and the remaining weight may be assigned with the weight 0.

Figure 5B:
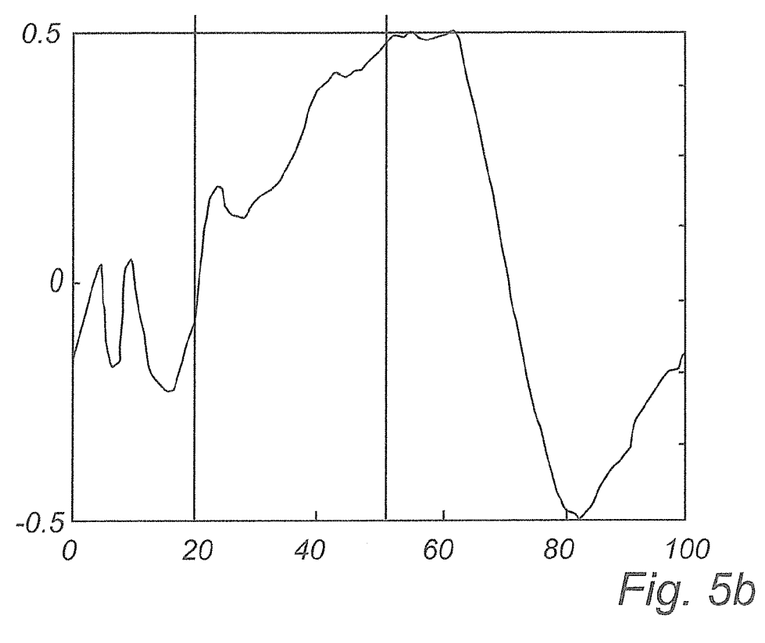

The inventor has shown that the resulting integral value RDI calculated as described above provides a good measure of the dyssynchronicity of the heart of a patient. In FIG. 5a, the $V_{Diff}$ is shown for a patient suffering from LBBB (Left Bundle Branch Block) without any cardiac resynchronisation therapy. To calculate the RDI value, the $V_{Diff}$ waveform is integrated during the most significant part of systole indicated by the vertical lines 50 and 51. As a comparison, the RDI value for the same patient during cardiac resynchronisation therapy is shown in FIG. 5b. The RDI value for the situation in FIG. 5a, i.e. without CRT, is 12.2 and the RDI value in the situation in FIG. 5b, i.e. at CRT, is 7.7, in other words, a reduction by 37% of the RDI value. Measurements made by means of echo-cardiography shows a reduction in "time from QRS to peak systolic movement of the posterior wall" from 350 ms to 270 ms, which corresponds to a reduction by 23%. A reduction of in the difference between pulmonary pre-ejection delay and aortic pre-ejection period with roughly 60 ms was also observed.

Further, in table 1 below, changes of the RDI value are compared with reductions in dyssynchronicity (defined as the difference between pulmonary pre-ejection delay and aortic pre-ejection period) for three different patients. Measurements were performed on patients 1-3 without cardiac resynchronisation therapy (CRT) and with CRT.

TABLE 1

| Patient | Dyssyn. no CRT | Dyssyn. with CRT | Change | RDI no CRT | RDI with CRT | Change |
|---|---|---|---|---|---|---|
| 1 | 60 ms | 0 ms | −60 ms | 12.2 | 7.7 | −4.5 |
| 2 | 29 ms | 21 ms | −8 ms | 7.6 | 5.9 | −1.7 |
| 3 | 111 ms | 95 ms | −16 ms | 13.0 | 12.4 | −0.6 |

Figure 6:
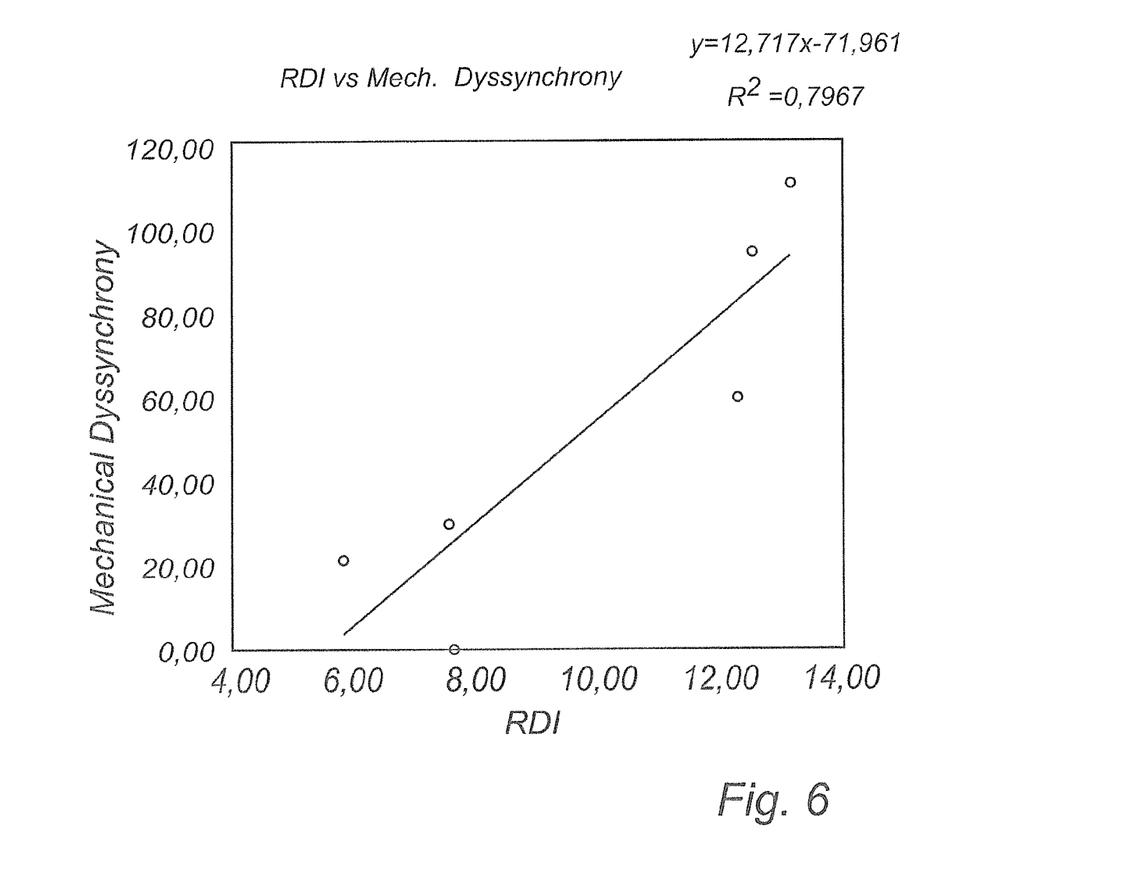
FIG. 6 shows the linear relationship between the dyssynchronicity measure and measured dyssynchronicity (at three patients where the mechanical dyssynchronicity is measured by means of echo-cardiography).

As can be seen from table 1, the RDI value effectively captures the reduction of dyssynchronicity in the three different patients and the magnitude of the reduction of the RDI value corresponds to the magnitude of reduction of the measure dyssynchronicity. For example, for patient 2, the measured dyssynchronicity is reduced by 28% and the corresponding the RDI value is reduced by 23%. It can be noted that the RDI measure sorts these patients after the "effect" of the CRT. In FIG. 6, the linear relationship between the RDI parameter and the measured mechanical dyssynchronicity (echo cardiography) is shown. As can be seen, there is a high correlation, r=0.9, between the RDI parameter and the measured dyssynchronicity.

Figure 8:
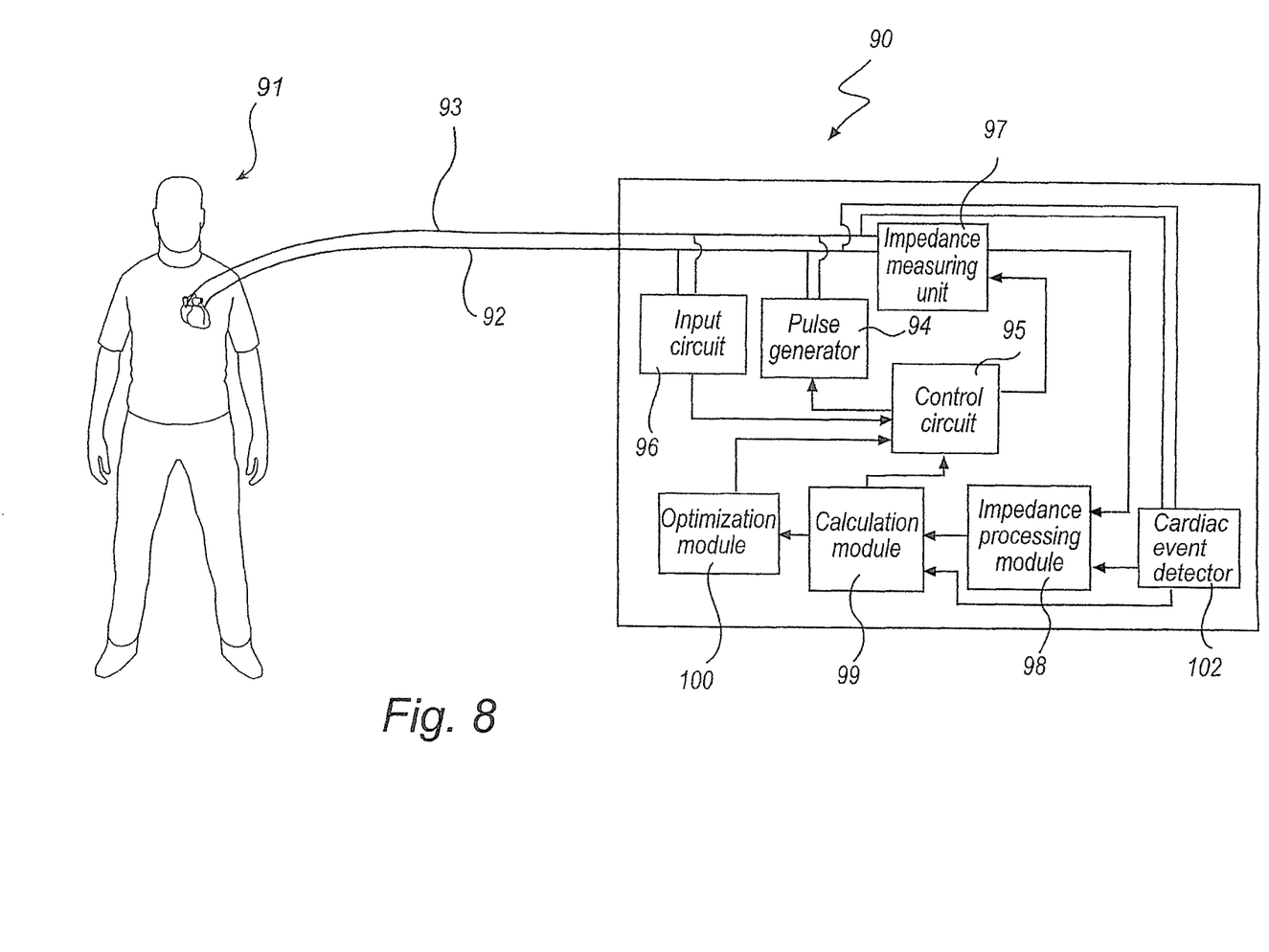
FIG. 8 is a functional block diagram form of an embodiment of a medical device according to the present illustrating basic circuit elements that may provide, for example, pacing stimulation in the heart and particularly illustrating components for calculating a dyssynchronicity measure according to the present invention.

Turning now to FIG. 8, another embodiment of the present invention will be discussed. In this embodiment, the present invention is implemented in an extracorporeal device located, for example, in a care institution, which device may be connected to the heart of a patient by means of catheters. Thereby, it is possible, for example, during a preparation for an implantation procedure (e.g. of an implantation of an implantable medical device according to the present invention) to scan for responders to cardiac resynchronization therapy.

In FIG. 8, an extracorporeal device 90 is connected to a patient 91 via catheter leads 92, and 93 each comprising one or more electrodes, such a coils, tip electrodes or ring electrodes, arranged to, inter alia, transmit pacing pulses for causing depolarization of cardiac tissue adjacent to the electrode (-s) generated by a pace pulse generator 94 under influence of a control circuit 95 comprising a microprocessor and for measuring impedances reflecting the septal wall movements. The control circuit 95 controls, inter alia, pace pulse parameters such as output voltage and pulse duration. A memory circuit (not shown) may be connected to the control circuit 95, which memory circuit may include a random access memory (RAM) and/or a non-volatile memory such as a read-only memory (ROM). The memory circuit may however be an external unit outside the extracorporeal device 90. Detected signals from the patient's heart are processed in an input circuit 96 and are forwarded to the microprocessor of the control circuit 95 for use in logic timing determination in known manner. An impedance measuring unit 97 is adapted to carry out impedance measurements of the intra-cardiac impedance of the patient, for example, by means of applying a current over a RV ring electrode and a LV ring electrode to measure impedance signals substantially reflecting mechanical activity on the left side of the heart. The resulting voltage is, according to these examples, measured between a RV tip electrode and a LV tip electrode. In order to carry out impedance measurements of the intra-cardiac impedance of the patient substantially reflecting mechanical activity on the right side of the heart, a current may be applied over a RV ring electrode and a RV tip electrode. The resulting voltage may be measured between the same electrode pair. The raw impedance data is then supplied to an impedance processing module 98, which may comprise, for example, amplifiers and filters e.g. FIR or IIR filters. The impedance processing module 98 may further be adapted to perform, for example, amplitude normalizing and time synchronization of the measured impedances. Moreover, the impedance sets may also be subjected to a rectifying step in the impedance processing module 98. A calculation module 99 is adapted to calculate a measure of a dyssynchronicity based on a resulting parameter from a comparison between at least a subset of the first and the second impedance sets, respectively, which subsets contain information of the mechanical systole. In one embodiment, the calculation module 47 is adapted to calculate the resulting parameter between the first and the second sets of impedances as a difference value parameter set related to a morphology of the impedance sets, which difference value parameter set forming a waveform over the at least a part of a cardiac cycle, to integrate the waveform over a predetermined period of time of the part of a cardiac cycle to obtain an integral value, the predetermined period of time corresponding to a predetermined part of mechanical systole; and to determine the dyssynchrony measure to correspond to the integral value. Furthermore, a cardiac event detector 102 is connectable to the electrodes, for example, a RV tip electrode, a RV ring electrode, a LV tip electrode, and a LV ring electrode via the catheter leads 92 and 93, and is connected to the impedance processing module 98 and the calculation module 99. The cardiac event detector 102 is adapted to detect the occurrence of cardiac events in the cardiac cycle. In one embodiment, the cardiac event detector 102 is adapted to identify a first predetermined event of the cardiac cycle, for example, the R-wave of a cardiac cycle, indicating a first activation of the left or the right ventricle. Further, a second cardiac event, for example, the T-wave of the cardiac cycle may be identified. The calculation module 99 is adapted to determine a period of the cardiac cycle in relation to the identified events in the cardiac cycle over which the resulting parameter is calculated. In one embodiment, as will be explained in detail below, a dyssynchronicity measure is calculated by integration of the resulting parameter over a part of a cardiac cycle, which part corresponds to the most significant part of the mechanical systole. Empirically, this significant part has been found to be in the range between 20-50% of the heart cycle following the activation of the primary ventricle. In another embodiment, the period of time between a detection of the R-wave and the detection of the T-wave is used for the calculation of the dyssynchronicity measure, a period that also has been shown to comprise the significant part of mechanical systole. This will be described in more detail below with reference to FIG.

4. This embodiment of the present invention may be used to check whether a specific patient responds to cardiac resynchronization therapy (CRT) before a CRT device actually is implanted. That is, it can be evaluated whether a patient suffering from, for example, LBBB (Left Bundle Branch Block) causing a dyssynchronous mechanical activity of the heart responds to CRT by introducing the catheters 92 and 93 into the heart and applying therapy using the pulse generator 94 and control circuit 95 of the extracorporeal device 90. By obtaining the dyssynchronicity measure for each cardiac cycle, or as an average of a number of cardiac cycles, it can be checked whether the patient responds to the therapy. Further, if it is found that the patient responds to therapy, the CRT parameters can be optimized or fine-tuned. For example, a VV-interval may be optimized. For this purpose, the extracorporeal device 90 may further comprise an optimization module 100 connected to the calculation module 99 and the control circuit 95. In one embodiment of the present invention, a VV-interval is optimized based on the dyssynchronicity measure, wherein the dyssynchronicity measure is minimized. The pulse generator 94 is instructed to adapt the VV-interval in accordance with the optimization. In another embodiment, the optimization module 100 is adapted to compare a present dyssynchronicity measure with preceding dyssynchronicity measures to obtain a trend of the dyssynchronicity measure and/or with a reference dyssynchronicity measure to identify and to determine whether a present VV-interval should be extended or shortened based on the comparison. The pulse generator 94 is instructed to adapt a present VV-interval in accordance with the determined extension or shortening of the VV-interval. For example, a reference measure may be obtained for a patient in connection with the implantation of the device during synchronized ventricular activity.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

I claim as my invention:

1. A medical device for determining a dyssynchronicity measure indicating a degree of mechanical dyssynchronicity of a heart of a patient, said medical device being connectable to at least two medical leads each having electrodes adapted to be positioned within or at said heart, said medical device comprising:
    an impedance measuring unit configured to measure:
        a first intracardiac impedance set over at least one cardiac cycle using a first electrode vector/array having at least two electrodes placed such that said first intracardiac impedance set substantially reflects a mechanical activity of a left side of the heart; and
        a second intracardiac impedance set over at least one cardiac cycle using a second electrode vector/array having at least two electrodes placed such that said second intracardiac impedance set substantially reflects a mechanical activity of a right side of the heart; and
    a calculating module configured to calculate a measure of a dyssynchronicity based on a resulting parameter from a comparison between at least a subset of said first and said second impedance sets, respectively, said subsets containing information of mechanical systole;
    wherein said calculating module is adapted to:
        calculate the resulting parameter between said first and said second sets of impedances as a difference value parameter set related to a morphology of said impedance sets, said difference value parameter set forming a waveform over at least a part of a cardiac cycle;
        integrate said waveform over a predetermined period of time of said part of a cardiac cycle to obtain an integral value, said predetermined period of time corresponding to a predetermined part of mechanical systole; and
        determine said dyssynchrony measure to correspond to said integral value.

2. The medical device according to claim 1, further comprising:
    a QRS detector circuit connectable to said electrodes, said QRS detector being configured to detect occurrence of cardiac events in the cardiac cycle, said QRS detector circuit being adapted to identify at least a first predetermined event of the cardiac cycle.

3. The medical device according to claim 1, further comprising an optimization module configured to:
    optimize a VV-interval based on said dyssynchronicity measure, wherein said dyssynchronicity measure is minimized; and
    instruct a pulse generator to adapt the VV-interval in accordance with the optimization.

4. A medical device for determining a dyssynchronicity measure indicating a degree of mechanical dyssynchronicity of a heart of a patient, said medical device being connectable to at least two medical leads each having electrodes adapted to be positioned within or at said heart, said medical device comprising:
    an impedance measuring unit configured to measure:
        a first intracardiac impedance set over at least one cardiac cycle using a first electrode vector/array having at least two electrodes placed such that said first intracardiac impedance set substantially reflects a mechanical activity of a left side of the heart; and
        a second intracardiac impedance set over at least one cardiac cycle using a second electrode vector/array having at least two electrodes placed such that said second intracardiac impedance set substantially reflects a mechanical activity of a right side of the heart;
    a calculating module configured to calculate a measure of a dyssynchronicity based on a resulting parameter from a comparison between at least a subset of said first and said second impedance sets, respectively, said subsets containing information of mechanical systole; and
    an impedance processing module configured to synchronize said first and second impedance sets in relation to a predetermined cardiac event;
    wherein said impedance processing module is configured to assign a predetermined weight to each impedance value in said first and second set of impedances or to each value in the a difference value parameter set.

5. The medical device according to claim 4, wherein said impedance processing module is adapted to perform an amplitude normalizing procedure on the first and second impedance sets.

6. The medical device according to claim 4, wherein the calculation module is configured to rectify the individual impedance values of the first and second set of impedance values or in a difference value parameter set.

7. A method for determining a dyssynchronicity measure in a medical device, said dyssynchronicity measure indicating a degree of mechanical dyssynchronicity of a heart of a patient, said medical device being connectable to at least two medical leads each having electrodes adapted to be positioned within or at said heart, said method comprising:

measuring a first intracardiac impedance set over at least one cardiac cycle using a first electrode vector/array having at least two electrodes placed such that said first intracardiac set substantially reflects a mechanical activity of a left side of the heart;

measuring a second intracardiac impedance set over at least one cardiac cycle using a second electrode vector/array having at least two electrodes placed such that said second intracardiac impedance set substantially reflects a mechanical activity of a right side of the heart; and calculating a measure of a dyssynchronicity based on a resulting parameter set from a comparison between at least a subset of said first and said second impedance sets, respectively, said subsets containing information of a mechanical systole;

wherein said calculating comprises:
calculating the resulting parameter between said first and said second sets of impedances as a difference value parameter set related to a morphology of said impedance sets, said difference value parameter set forming a waveform over at least a part of a cardiac cycle;

integrating said waveform over a predetermined period of time of said part of a cardiac cycle to obtain an integral value, said predetermined period of time corresponding to a predetermined part of mechanical systole; and determining said dyssynchrony measure to correspond to said integral value.

8. The method according to claim 7, further comprising synchronizing said first and second impedance in relation to a predetermined cardiac event.

9. The method according to claim 8, wherein said processing further comprises performing an amplitude normalizing procedure on the first and second impedance sets.

10. The method according to claim 7, further comprising:
detecting occurrence of cardiac events in the cardiac cycle; and
identifying at least a first predetermined event of the cardiac cycle.

11. A method for determining a dyssynchronicity measure in a medical device, said dyssynchronicity measure indicating a degree of mechanical dyssynchronicity of a heart of a patient, said medical device being connectable to at least two medical leads each having electrodes adapted to be positioned within or at said heart, said method comprising:

measuring a first intracardiac impedance set over at least one cardiac cycle using a first electrode vector/array having at least two electrodes placed such that said first intracardiac set substantially reflects a mechanical activity of a left side of the heart;

measuring a second intracardiac impedance set over at least one cardiac cycle using a second electrode vector/array having at least two electrodes placed such that said second intracardiac impedance set substantially reflects a mechanical activity of a right side of the heart; and calculating a measure of a dyssynchronicity based on a resulting parameter set from a comparison between at least a subset of said first and said second impedance sets, respectively, said subsets containing information of a mechanical systole;

wherein said processing a resulting parameter set comprises assigning a predetermined weight to each impedance value in said first and second set of impedances or to each value in a difference value parameter set.

12. The method according to claim 11, wherein said assigning comprises rectifying the individual impedance values of the first and second set of impedance values or of a difference value parameter set.

13. The method according to claim 12, further comprising:
optimizing a VV-interval based on said dyssynchronicity measure, wherein said dyssynchronicity measure is minimized and a pulse generator is instructed to adapt the VV-interval in accordance with the optimization.

* * * * *